United States Patent [19]

Anderson

[11] Patent Number: 4,806,561

[45] Date of Patent: Feb. 21, 1989

[54] METHOD OF TREATMENT OF SOLID CANCER TUMOR OF THE COLON OR BREAST USING PYRROLE DERIVATIVE

[75] Inventor: Wayne K. Anderson, Williamsville, N.Y.

[73] Assignee: The Research Foundation of State University of New York, Albany, N.Y.

[21] Appl. No.: 804,239

[22] Filed: Dec. 3, 1985

Related U.S. Application Data

[63] Continuation of Ser. No. 378,276, May 14, 1982, abandoned.

[51] Int. Cl.$^4$ .............................................. A61K 31/40
[52] U.S. Cl. ...................................................... 514/427
[58] Field of Search .......................................... 514/427

[56] References Cited

PUBLICATIONS

Grant Applns. CA 22935-01 through -06, Vinylogous Carbinolamine Tumor Inhibitors (Principal Investigator: Wayne K. Anderson) Publication in Jun., 1982 issue of Cancer Research (Anderson).
Cancer Treatment Reports, vol. 66, No. 1, Jan. 1982 (Wayne K. Anderson).
Jour. Med. Chemistry, 1979, 22, 977 (Anderson).
Jour. Med. Chemistry, 1980, 23, 87 (Anderson).
Jour. of Heterocyclic Chemistry, 1980, 17, 513 (Anderson).
Jour. Organic Chemistry, 1977, 42, 599 (Anderson).
Jour. Med. Chemistry, 1977, 20, 812 (Anderson).
Jour. Med. Chemistry, 1977, 20, 1691 (Anderson).

*Primary Examiner*—Jerome D. Goldberg
*Attorney, Agent, or Firm*—William J. Crossetta; Michael L. Dunn

[57] ABSTRACT

This invention provides a method of providing treatment to a warm blooded animal in need of treatment of a solid cancer tumor of the colon or breast comprising administering an effective amount of a pyrrole of the formula:

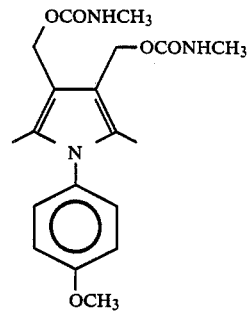

9 Claims, No Drawings

METHOD OF TREATMENT OF SOLID CANCER TUMOR OF THE COLON OR BREAST USING PYRROLE DERIVATIVE

The invention described herein was made in the course of work under a grant or award from the Department of Health Education and Welfare.

This application is a continuation of Ser. No. 378,276, filed May 14, 1982, now abandoned.

BACKGROUND OF THE INVENTION

This invention relates to a pharmaceutical compound found particularly suitable for inhibiting growth of solid tumors of the colon or breast in warm blooded animals.

PRIOR ART

There has been a continuing search for treatment for solid cancer tumors of the colon or breast in warm blooded animals and especially in human beings. The search for effective, stable and non-toxic treatment materials continues as control of solid cancer tumors of the colon or breast has not been particularly well achieved by prior materials. There is a particular need for materials which will be effective against solid tumors of the colon and breast.

The chemistry of formation of pyrrole compounds has been disclosed in several papers co-authored by Dr. Wayne K. Anderson. Some of these papers also detail the activity of many of the compounds against leukemic cancers and leukemic tumors. These papers concerning the formation of pyrrole compounds are as follows:

1. Anderson, W. K.; Corey, P. F. *J. Org. Chem.* 1977, 42, 559. "1,3-Dipolar Cycloaddition Reactions with Isatin-N-acetic Acids: Synthesis of Dimethyl 9-Oxo-9H-pyrrolo[1,2-a]indole-1,2-dicarboxylates."
2. Anderson, W. K.; Corey, P. F. *J. Med. Chem.* 1977, 20, 812. "Synthesis and Antileukemic Activity of Diacetate and bis(N-Alkylcarbamate) Derivatives of 5-Substituted 2,3-Dihydro-6,7-bis(hydroxymethyl)-H-pyrrolizines."
3. Anderson, W. K.; Corey, P. F. *J. Med. Chem.* 1977, 20, 1691. "Antileukemic Activity of Derivatives of 1-Phenyl-2,5-dimethyl-3,4-bis(hydroxymethyl)-pyrrole Bis(N-methylcarbamate)."
4. Anderson, W. K.; Halat, M. J. *J. Med. Chem.* 1979, 22, 977. "Antileukemic Activity of Derivatives of 1,2-Dimethyl-3,4-bis(hydroxymethyl)-5-phenyl-pyrrole Bis(N-methylcarbamate)."
5. Anderson, W. K.; Halat, M. J.; Rick, A. C. *J. Med. Chem.* 1980, 23, 87. "Synthesis and Antileukemic Activity of 1-Methyl-2,5-diphenyl-3,4-bis(hydroxymethyl)-, 1,2,3-Triphenyl-4,5-bis(hydroxymethyl)-, and 1-Methyl-2,3-diphenyl-4,5-bis(hydroxymethyl)-pyrrole Bis(N-methylcarbamate)."
6. Anderson, W. K.; McPherson, H. J., Jr.; New, J. S. *J. Heterocycl. Chem.* 1980, 17, 513. "The Synthesis of Polycyclic Benz-Fused Pyrroles."
7. Anderson, W. K.; New, J. S.; Corey, P. F. *Arzneim.-Forsch.* 1980, 30 (I), 765. "Vinylogous Carbinolamine Tumor Inhibitors. 7. Tumor Inhibitory Agents: bis-(N-alkylcarbamate) derivatives of 2,3-dihydro-5-(3',4'-dichlorophenyl)-6,7-bis(hydroxymethyl)-1H-pyrrolizine."

The last paper entitled "Vinylogous Carbinolamine Tumor Inhibitors" is of particular interest as compounds related to the pyrrole derivative of the invention is disclosed therein and indicated as effective for leukemic cancers.

As is well known in the cancer therapy field, the treatment of solid tumor cancers is more difficult than treatment of leukemic tumor cancers particularly those solid tumors of the breast or colon. Experience has shown that effectiveness against leukemia is not in any way an assurance of the effectiveness against solid tumors.

Therefore, there remains a need for compounds suitable for treatment of solid cancer tumors.

BRIEF DESCRIPTION OF THE INVENTION

An object of this invention is to overcome difficulties of the prior art.

Another object of this invention is to provide improved treatment of solid cancer tumors of the colon or breast.

These and other objects of the invention are generally accomplished by administering sufficient pyrrole derivative having the formula:

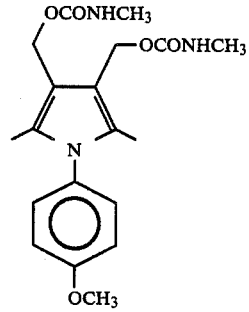

The quantity of the pyrrole derivative sufficient for treatment of cancer tumors of the colon or breast varies both depending upon the size of the warm blooded animal involved, upon the type of solid tumor and upon the species of the animal involved. In general for most applications, between about 6 milligrams per kilogram of body weight to about 400 milligrams per kilogram of body weight of the pyrrole derivative is suitable for use in accordance with the method of the invention. In general, large animals require less of any pharmaceutical compound per kilogram of body weight than smaller animals.

MODES OF PRACTICING THE INVENTION

The method of the invention has numerous advantages over prior treatment methods which will become clear from the specification as set forth below. A method of treatment utilizing the pyrrole derivative has a range of activity against tumors. This range also has activity over a broad range of doses. This makes the drug much more suitable for widespread use and also lowers the risk margin of a toxic dose being given.

As used herein the term leukemic cancer refers to all cancers or neoplasms of the hemopoietic and immune systems (blood and lymphatic system). The term solid tumors generally means those epithelial neoplasms, such as skin and stomach cancer; connective tissue neoplasms, such as bone and smooth muscle cancer; neoplasms of the nervous system; neoplasms of multiple tissues, such as breast cancer and kidney cancer and miscellaneous neoplasms such as placenta cancer and ovary cancer. Of particular interest herein are the solid cancer tumors of the colon and breast.

The solid tumors are believed more difficult to treat than leukemic cancers as they are slower growing and dense. It is believed that most treatment materials are effective at the time of cell division. The slower growth means fewer cell divisions and fewer opportunities for the treatment compound to affect the cell. The dense mass of tumor does not allow as ready access of the treatment compound to the tumor as the more widely separated cells of the leukemic blood cancers. Therefore, activity of the compounds of the invention against solid tumors of the colon and breast is unusual and of interest for solid tumor treatment.

The pyrrole derivative of the invention may be formed by any satisfactory method. The following is a suitable method:

A mechanically stirred solution of dry 4-methoxyacetanilide (0.25 mol) in anhydrous toluene (500 mL) was treated with NaH (57% oil dispersion, 11.57 g, 0.28 mol) and heated under reflux for 2 h (hours). Ethyl 2-bromopropionate (37.5 mL, 0.29 mol) was added and the mixture was refluxed for 2 h. The cooled mixture was centrifuged to facilitate separation of the NaBr and filtered, and the toluene solution was evaporated to dryness in vacuo. The syrupy residue was dissolved in ethanol (300 mL), a solution of NaOH (20 g) in water (30 mL) was added, and the mixture was heated under reflux for 1 h. The cooled solution was concentrated in vacuo, water (700 mL) was added, and the mixture was extracted with $CH_2Cl_2$ (2×200 mL). The mixture was acidified to pH 1 with concentrated HCl, the precipitate which formed was collected and crystallized from ethanol-water to give N-acetyl-N-(4-methoxyphenyl)alanine in 70% yield: mp (melting point) 197°–201° C.

A solution of N-acetyl-N-(4-methoxyphenyl)alanine (0.10 mol) in acetic anhydride (100 mL) and dimethyl acetylenedicarboxylate (DMAD, 50 mL, 0.40 mol) was stirred in a flask equipped with a reflux condenser and a gas bubbler to monitor $CO_2$ evolution during the reaction. The mixture was heated to 65° C. (bath temperature) over a 15-min period and maintained at this temperature for 1 h after the rate of gas evolution had substantially decreased. The mixture was concentrated to dryness in vacuo and the syrupy residue was crystallized from methanol-water to give the product (98% yield): mp 75°–76° C.

N-(4-Methoxyphenyl)-2,5-dimethyl-3,4-bis(hydroxymethyl)pyrrole.

A solution of dimethyl N-(4-methoxyphenyl)-2,5-dimethylpyrrole-3,4-dicarboxylate (0.04 mol) in dry dichloromethane (50 mL) was added dropwise over a 15-min period to a mechanically stirred mixture of lithium aluminum hydride (3.4 g, 0.08 mol) in anhydrous ether (100 mL) heated under reflux (50°–55° C. bath). The stirred mixture was heated under reflux for 1 h after the addition was complete and then cooled in an ice bath. The excess hydride was carefully decomposed with small additions of wet ether and then with water until the salts were white. The mixture was filtered (medium-porosity sintered-glass funnel) and the inorganic residue was washed with several portions of hot dichloromethane (about 30 mL) until the total filtrate volume was about 400 mL. The filtrate was concentrated in vacuo to a volume of about 125 mL, warmed to boiling, and diluted with slow portionwise addition of petroleum ether (about 100 mL) to yield 91% of N-(4-methoxyphenyl)-2,5-dimethyl-3,4-bis(hydroxymethyl)pyrrole: mp 143°–145° C. (dec).

N-(4-Methoxyphenyl)-2,5-dimethyl-3,4-bis(hydroxymethyl)pyrrole Bis(N-methylcarbamate).

A cooled (about 10° C.) stirred solution of N-(4-methoxyphenyl)-2,5-dimethyl-3,4-bis(hydroxymethyl)pyrrole (0.01 mol) in dichloromethane (25 mL) containing triethylamine (0.25 mL) was treated with methyl isocyanate (3.0 mL, 0.05 mol) and then heated under reflux (50° C. bath) for 2 h. The solution was cooled and concentrated to dryness in vacuo and the solid residue was dissolved in hot ethyl acetate and filtered. The filtrate was concentrated in vacuo to about 25 mL, heated to boiling, and carefully diluted with portionwise additions of hot isopropyl ether (about 75 mL) to yield, upon cooling, 76% of N-(4-methoxyphenyl)-2,5-dimethyl-3,4-bis(hydroxymethyl)pyrrole Bis(N-methylcarbamate): mp 156°–158° C. (dec).

The general synthesis of these compounds is set forth in the paper entitled "Antileukemic Activity Of 1-Phenyl-2,5-dimethyl-3,4-bis(hydroxymethyl)pyrrole Bis(N-methylcarbamate)", *J. Med. Chem.*, 1977, Vol. 20, No. 12, pp. 1691–1694.

Any suitable dosage may be given in the method of the invention. The type of and the amount of dosage will vary widely depending on the species of the warm blooded animal, body weight and tumor being treated. Generally, a dosage of between about 6 milligrams per kilogram of body weight and about 400 milligrams per kilogram of body weight is suitable. Generally, the dosage in man for solid cancer tumors of the colon, lung, or breast is lower than for small warm blooded mammals such as mice.

The method of treatment may be any suitable method which is effective in treatment of the particular solid tumor which is under treatment. A method of applying an effective amount also varies depending on the tumor being treated. It is believed that treatment by intravenous application formulated with an appropriate carrier to facilitate intravenous application will be the suitable method of administering the pyrrole derivative in man.

The following tests demonstrate the surprising effectiveness of the treatment of the invention.

EXAMPLES

Tumor cells were inoculated ip (intraperitoneal) into male $CDF_1$ mice, unless otherwise noted, in the B16, and colon tumor 26 assays. The tumors in the $CD8F_1$ and colon tumor 38 assays were implanted sc (subcutaneously) in male $CDF_1$ and female $BDF_1$ mice, respectively. Tumor cells were injected iv (intravenously) into female $BDF_1$ mice in the Lewis Lung tumor (LL). Six to ten animals were used in each test group, and 40 untreated animals were used in the control groups. In the survival models (B16, colon tumor 26, and LL) as well as in the tumor weight (estimated from tumor diameters) models ($CD8F_1$ and colon tumor 38), results are expressed as a percentage of the test animal evaluation (T) compared to that for the controls (C) and are reported as %T/C; these values are based on all mice, not just dying mice.

The test animal evaluation (T) for mice in survival models when compared to the control group (C) of mice provides a comparison of the number of the mice surviving the test with treatment as opposed to the test group where treatment was not given. Therefore, a high % T/C number indicates the treatment was effective in survival tests. In the tumor weight tests, the test animal evaluation (T) provides an estimate of the tumor weight in treated mice and compares it to the estimated tumor weight in the untreated control mice. In the tumor weight test, a low % T/C indicates effective treatment as the tumors on treated mice are smaller than tumors on the untreated control mice. The test compounds were administered ip as suspensions; the vehicles was hdroxypropylcellulose (Kluccl).

The dose in any given assay is defined as toxic if any of the test animals die within the first 5 days of the test, unless otherwise specified (Tables 1–4). Test animal weight changes are noted in parentheses, and these data may be regarded as an indication of continuing drug toxicity. The weight change data are expressed as T−C (test animal weight change minus control animal weight change, in g).

TABLE 1

−% T/C in CD8F$_1$* Mammory Solid Tumor+

| Dose (mg/kg) | |
|---|---|
| 200 | Toxic |
| 100 | 1(−6.9) |
| 50 | 45(−4.1) |
| 25 | 86(−3.2) |
| 12.5 | 47(−1.2) |
| 6.25 | 121(−0.8) |

*Tumor homogenate containing approximately 5 × 10$^6$ cells was inoculated sc into male CD8F$_1$ mice; 5 doses of a compound were given ip beginning 24 hrs after tumor inoculation and, thereafter, every 7 days. Dose was defined as toxic if all test animals failed to survive the 30-day test. Values in parentheses = T − C, weight change in g.
+Female CDF$_1$ mice were used in this assay.

TABLE 2

−% T/C in colon 38 tumor*+

| Dose (mg/kg) | |
|---|---|
| 200 | 49(−8.2) |
| 100 | 93(−4.9) |
| 50 | 111(−2.8) |
| 25 | 70(−1.9) |
| 12.5 | 125(−1.3) |
| 6.26 | 82(−0.1) |

*A tumor fragment was implanted sc in female BDF$_1$ mice; 1 dose of a compound was given ip 2 days after tumor implantation, and another was given 7 days later. Dose was defined as toxic if all test animals failed to survive the 20-day test. Values in parentheses = T − C, in g.

TABLE 3

−% T/C in B16-Solid Tumor*

| Dose (mg/kg) | |
|---|---|
| 100 | 50(−2.9) |
| 50 | 111(−1.2) |
| 25 | 140(−1.1) |
| 12.5 | 136(−0.7) |
| 6.25 | 133(−0.6) |
| 3.12 | 112(−0.3) |

*Tumor homogenate (0.5 ml, prepared from a homogenized mixture of 1 g of tumor and 10 ml of balanced salt solution) was inoculated ip; 9 daily doses of a compound were given ip beginning 24 hrs after tumor inoculation. Values in parentheses = T − C, in g.
Female B6C3F$_1$ mice were used in this assay.

TABLE 4

−% T/C in LL-Solid Lung Tumor*

| Dose (mg/kg) | |
|---|---|
| 100 | Toxic |
| 50 | 100(−2.5) |
| 25 | 102(−0.7) |

TABLE 4-continued

−% T/C in LL-Solid Lung Tumor*

| Dose (mg/kg) | |
|---|---|
| 12.5 | 104(−0.5) |
| 6.25 | 104(−0.1) |
| 3.12 | 106(−0.3) |

*Ascitic fluid containing approximately 10$^5$ cells was injected iv into female BDF$_1$ mice; 9 daily doses were given ip, beginning 24 hrs after tumor inoculation. Values in parentheses = T − C, in g.

The administration of the compound of the invention resulted in cures of the CD8F$_1$ tumor in the instance of three of the ten mice that received the 100 milligrams per kilogram of body weight. It can also be seen that the compound of the invention was particularly effective against the colon tumor 38. Taken together, the results indicate a high level of effectiveness against a wide range of solid tumors and special effectiveness against colon tumors.

While the specification only illustrates the effectiveness of the compounds against tumors implanted in mice, it is also within the invention to utilize the treatment for all warm blooded animals, particularly treatment of mammals is contemplated.

What is claimed is:

1. A method of inhibiting the growth, in a warm blooded animal, of a solid cancer tumor of the colon, lung, or breast susceptible to a pyrrole of the formula:

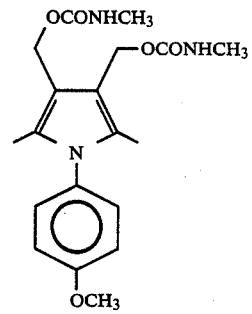

comprising parenterally administering to said warm blooded animal, in vivo, an effective solid cancer tumor inhibiting amount of said pyrrole.

2. The method of claim 1 wherein the quantity of said pyrrole administered is between about 6 and about 400 milligrams per kilogram of body weight of the warm blooded animal.

3. The method of claim 1 wherein said warm blooded animal is a mammal.

4. The method of claim 3 wherein said pyrrole is administered intravenously.

5. The method of claim 3 wherein said pyrrole is administered subcutaneously.

6. The method of claim 3 wherein an effective amount of said pyrrole is administered intraperitoneally.

7. The method of claim 3 wherein said effective amount of pyrrole is administered with a carrier material.

8. A method of providing treatment to a warm blooded animal in need of treatment of a solid cancer tumor of the colon or breast comprising parenterally administering to said warm blooded animal an effective solid cancer tumor inhibiting amount of a pyrrole of the formula:

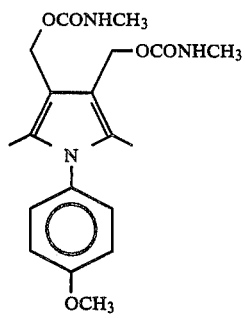

9. A pharmaceutical preparation adapted for parenteral administration in a warm blooded animal to inhibit the growth of a solid cancer tumor of the colon, lung, or breast, in vivo, comprising, per dosage unit, a solid cancer tumor inhibiting effective non-toxic amount, within the range of 6 to about 400 milligrams per kilogram of body weight of the warm blooded animal being administered, of a pyrrole of the formula:

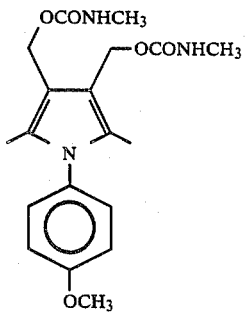

and a pharmaceutical diluent.

* * * * *

UNITED STATES PATENT AND TRADEMARK OFFICE
CERTIFICATE OF CORRECTION

PATENT NO. : 4,806,561
DATED : February 21, 1989
INVENTOR(S) : Wayne K. Anderson It is certified that error appears in the above-identified patent and that said Letters Patent is hereby corrected as shown below:

Column 7, Claim 9, line 17, after "colon" <u>delete</u> ", lung,".

Signed and Sealed this

Fifth Day of September, 1989

Attest:

DONALD J. QUIGG

Attesting Officer

Commissioner of Patents and Trademarks